United States Patent [19]
Diamond

[11] 3,987,116
[45] Oct. 19, 1976

[54] ETHYNYLARYL COMPOUNDS AND DERIVATIVES THEREOF

[75] Inventor: Julius Diamond, Lafayette Hill, Pa.

[73] Assignee: William H. Rorer, Inc., Fort Washington, Pa.

[22] Filed: Aug. 1, 1974

[21] Appl. No.: 493,591

Related U.S. Application Data

[62] Division of Ser. No. 306,061, Nov. 13, 1972, abandoned.

[52] U.S. Cl. .......................... 260/649 R; 260/473 F; 260/468 J; 260/469; 260/515 A; 260/611 F; 260/649 F; 260/650 R; 260/650 F; 260/668 R; 260/520 D; 424/340; 424/353

[51] Int. Cl.$^2$ .................... C07C 25/18; C07C 25/26

[58] Field of Search ........ 260/650 R, 650 E, 649 R, 260/649 F

[56] References Cited

UNITED STATES PATENTS

| | | | |
|---|---|---|---|
| 3,542,888 | 11/1970 | d'Ostrowick et al. | 260/668 R |
| 3,852,364 | 12/1974 | Diamond | 260/650 F |

OTHER PUBLICATIONS

Adams et al., Chem. Abstracts 38, 733[7] (1944).

*Primary Examiner*—D. Horwitz
*Attorney, Agent, or Firm*—James A. Nicholson

[57] ABSTRACT

Novel ethynylaryl compounds and derivatives are described. Their use in the treatment of inflammation is also disclosed.

7 Claims, No Drawings

ETHYNYLARYL COMPOUNDS AND DERIVATIVES THEREOF

This is a division of application Ser. No. 306,061, filed Nov. 13, 1972, and now abandoned.

SUMMARY OF THE INVENTION

This invention describes novel arylacetylenic compounds and derivatives and their use in therapeutic compositions. In addition, this invention describes the preparation of these arylacetylenic compounds and their derivatives. When the compounds of this invention are administered to mammals, they afford significant treatment for the relief of inflammation and associated pain and fever.

They further provide analgesic and antipyretic methods for the relief and treatment of pain and fever.

BACKGROUND OF THE INVENTION

Continued studies have been carried out during the last decade to develop drugs which would significantly inhibit the development of inflammation and relieve pain and fever as well as the pain and fever associated with inflammation. While much of this effort has been carried out in the steroid field, there have been compounds developed which are non-steroidal.

In particular, there have been many compounds developed as analgesic and/or anti-inflammatory agents which are characteristically described because they are acidic in nature. These compounds consist of an aromatic or partially aromatic ring system which has a side chain consisting of an alkanoic acid or carboxylic acid derivative thereof such as an ester, amide or salt. The ring system is one which is developed from hydrocarbon rings having at least one ring with aromatic properties and may include such as naphthalene, tetralin, phenanthrene, fluorene and the like. The ring system may further be substituted, however, the acid side chain function or derivative is necessary for activity. While many of these compounds have been found to be effective, they have had the drawback of causing various side effects, in particular, gastric hemorrhage and ulceration.

I have unexpectedly found a series of compounds which have ring systems similar to those described above and have a high degree of pharmacological activity, however, they do not have this characteristic acidic side chain which has heretobefore been described as essentially associated with analgesic and anti-inflammatory properties.

I have unexpectedly found that when the alkanoic acid side chain or derivative of these molecules is replaced by an ethynyl moiety, a group which is not a functional derivative of a carboxylic acid and which is chemically and physically unrelated, it unexpectedly results in compounds which have pronounced pharmacological properties and are unexpectedly useful for the relief and inhibition of inflammation conditions.

I have found that these ethynyl compounds are novel.

I have found that the compounds of this invention are effective in the treatment of inflammation and the control of arthritic conditions associated with inflammation without causing serious side effects.

I have further found that the compounds of this invention possess useful analgesic and antipyretic properties and are useful in the treatment of pain and/or fever without causing serious side effects.

I have also found an entirely novel class of pharmaceutical compositions which contain the compounds of this invention as active ingredients.

I have still further found a convenient method for synthesizing these compounds.

DESCRIPTION AND PREFERRED EMBODIMENTS

This invention comprises a class of chemical compounds which are effective for the relief and inhibition of inflammation and in the treatment of pain of fever. The compounds of this invention have the following generic formula I;

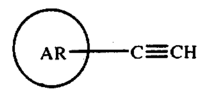

I.

where AR is a member consisting of 2–3 rings and having from 4 to 6 carbon atoms each of which at least one ring is aromatic or partially aromatic and said ring member may further be substituted.

More particularly, the preferred compounds of this invention are described by formula I where AR is

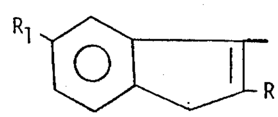

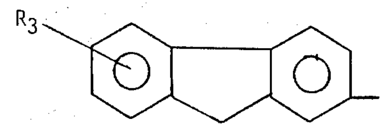

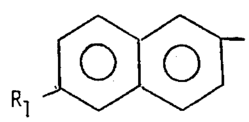

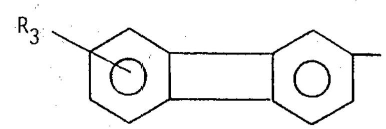

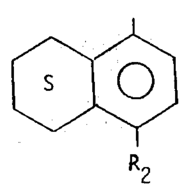

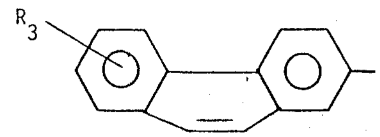

—Continued

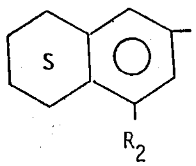

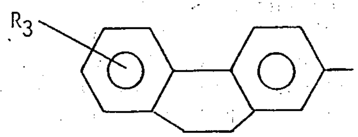

where

R is hydrogen or loweralkyl;

$R_1$ is loweralkoxy $R_2$ is halo; and $R_3$ is hydrogen or halo.

The more preferred compounds which may be used in the treatment of inflammation, pain and fever are described by formulae II–III;

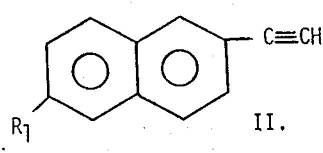

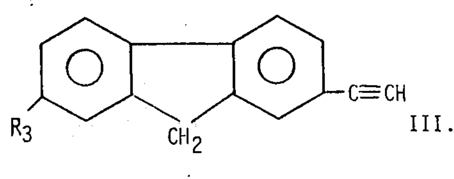

The most preferred compounds which may be used in the treatment of inflammation, pain and fever are described by formulae II–III where $R_1$ is methoxy and $R_3$ is hydrogen.

A special embodiment of this invention describes a class of novel chemical compounds which are described by formula I.

The more preferred compounds for this embodiment are described by formulae II and III.

The most preferred compounds are described by formulae II–III where $R_1$ is methoxy and $R_3$ is hydrogen.

In the descriptive portions of this invention, the following definitions apply:

"Alkyl" refers to a loweralkyl hydrocarbon group containing from 1 to 5 carbon atoms which may be straight chained or branched.

"Alkoxy" refers to a loweralkoxy group containing from about 1 to 5 carbon atoms which may be straight chained or branched.

The compounds of this invention may be prepared by the following general procedure:

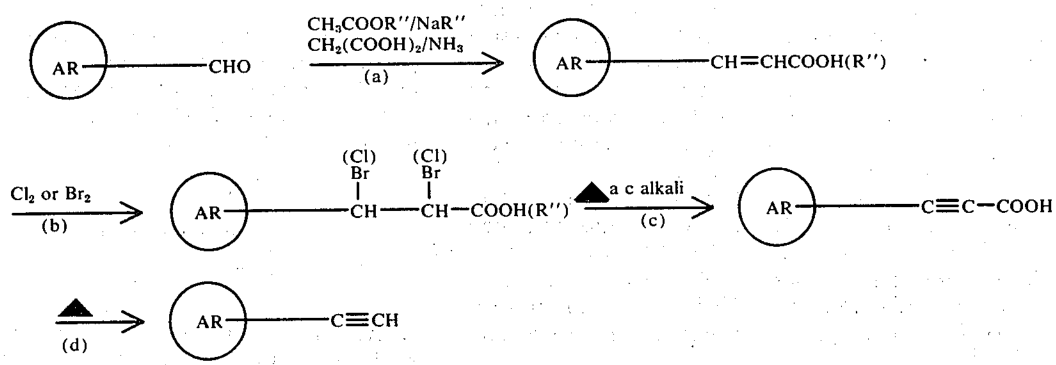

Claisen condensation of the proper arylaldehyde with an acetic acid ester (preferably a loweralkyl or benzyl ester) in the presence of a metal alkoxide results in a $\beta$-arylacrylic ester. The aldehyde may also be subjected to a Perkin reaction with acetic anhydride and an acetic acid salt or through a Knoevenogel condensation using malonic acid and ammonia in an amine base to obtain a $\beta$-arylacrylic acid (a). Addition to the double bond with halogen (preferably bromine) results in an $\alpha,\beta$-dibromopropilic acid or ester (b). When the $\alpha,\beta$-dibromopropionate is added to an alcoholic potassium hydroxide solution and heated for several hours the corresponding propiolic acid is prepared (c). Heating the propiolic acid at raised temperature in quinoline for 2–10 hours results in the desired acetylene compound (d).

A further preparation of the compound of this invention may be carried out as follows:

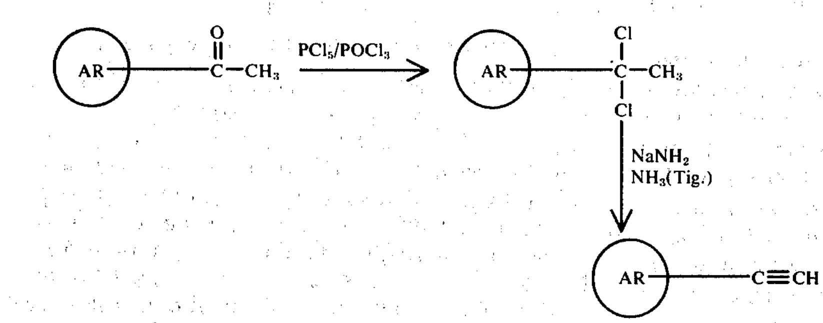

The carbonyl group of an arylacetone is reacted with a halogenating agent such as phosphorus pentochloride and phosphorus oxychloride is then dehalogenated using sodamide in liquid ammonia to obtain the desired acetylene.

The aldehyde starting materials of this invention are either known or they may be prepared of the following general procedures. References have been incorporated where necessary. It should be remembered, that when substitution is present in the ring moiety, one skilled in the art will of course use that sequence of reaction steps which will not conflict with the chemistry of the particular compound.

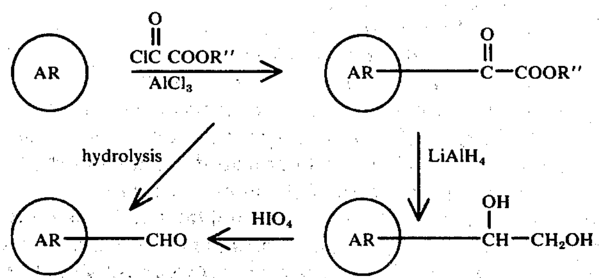

Condensation of the desired ring structure with a loweralkyl or aralkyl oxalyl chloride in the presence of anhydrous alumium chloride results in the corresponding glyoxylate. Reduction of the glyoxylate ester is then carried out with lithium aluminum hydride to give the 1,2-ethanediol. When this diol is treated with periodic acid the corresponding aldehyde is prepared. Alternatively, the glyoxylate ester may be converted to the glyoxylate acid by acid hydrolysis and the latter with heat is decarboxylated to the aldehyde.

I have found that the compounds of this invention exercise a useful degree of anti-inflammatory activity in mammals and are effective in the treatment of associated pain and fever and in the like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or antipyretic agent.

I have found that the compounds of this invention show a marked degree of analgesic activity and are effective in the relief of pain and fever. These compounds are essentially devoid of gastric hemorrhage side effects.

For all the above purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active acetylenic compounds may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example maize starch, alginic acid, etc., lubricating agents; for example, magnesium stearate, talc, etc., binding agents, for example, starch gelatin, etc., suspending agents; for example, methylcellulose, vegetable oil, etc., dispersing agents; for example, Tecithin, etc., thickening agents; for example, beeswax, hard paraffin, etc., emulsifying agents; for example, naturally occurring gums, etc., and non-irritating excipients; for example, cocoa butter and polyethylene glycols.

Various tests in animals can be carried out to show the ability of the acetylenic compounds of this invention to exhibit reactions that can be correlated with anti-inflammatory activity in humans. One such test is the carrageenan paw edema test, which shows the ability of the instant compounds to inhibit edema induced by injection of an inflammatory agent such as carrageenan into the tissues of the paw of a rat against non-inflammed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone, indomethacin and prednisolone. In view of the results of this test, the acetylenic compounds of this invention can be considered to be active anti-inflammatory agents.

A further test to show anti-inflammatory activity is the polyarthritis test in rats. This test is carried out on the animal model which closely resembles human arthritis and is widely used in the art. This is outlined by Winter and Nuss in *Arthritis and Rheumatism* 9: 394, (1966). In view of the results of this test, the acetylenic compounds of this invention can be considered to be active anti-inflammatory agents.

One method for measuring analgesic activity is the acetic acid writhing test as outlined by Siegmund et al in the *Proc. Soc. Exp. Biol. Med.* 95: 729–731, (1957). This method involves the intraperitoneal injection of 60 mg/kg of HOAc (0.6% solution; 0.1 ml/10 g) into male albino mice which produces a syndrone characterized by stretching movement. Analgesics prevent or suppress the stretch.

In view of the results of this test, the acetylenic compounds of this invention are considered to demonstrate non-narcotic analgesic activity.

One method of measuring gastric hemorrhage is as follows.

Albino male rats weighing 100-120 g are fasted for 24 hours but given free acess to water. The animals are placed in groups of 10 animals per dose and dosed by gastric gavage at a volume of 1 ml/100 g body weight with test compound suspended in 0.5% methylcellulose. Four hours after administration of compound, the animals are sacrificed and the rumens of the stomachs assayed for gastric hemorrhage. Hemorrhage is defined as an area of blood which is 1 mm or larger at the largest diameter. Diameter of the hemorrhage is recorded. The number of animals in each group with stomachs having at least one area of hemorrhage is recorded. The presence of areas of blood smaller than 1 mm, defined as petechiae, is noted but not counted in the assay. The percent hemorrhage for each group is statistically analyzed to determine the dose magnitude ($ED_{50}$)which causes production of gastric hemorrhage in 50% of the animals.

The following are detailed examples which show the preparation of the compounds of this invention. They are to be construed as illustrations of said compounds and are not intended to be limitations thereof.

EXAMPLE 1

β-(5-Methoxynaphth-2-yl)propenoic acid

5-Methoxynaphthalene-2-aldehyde (0.1 mole), malonic acid (0.2 moles), and dry pyridine (175 ml) are placed in a 1 l round-bottom flask. The malonic acid is dissolved by shaking on a steam bath and piperidine (0.5 ml) is added. The reaction is allowed to take place on the steam bath for 4 hours. After standing at room temperature overnight, the mixture is refluxed for 1 hour and cooled. The reaction mixture is poured into 250 ml of ice water and acidified with concentrated hydrochloric acid (80 ml) with stirring. The product is collected by filtration, washed with water (4 × 150 ml) and air dried to give β-(5-methoxynaphth-2-yl)propenoic acid.

When 5-methoxynaphthalene-2-aldehyde is replaced in the above example by the aldehydes of Table I below, then the corresponding product of Table II below is prepared.

Table I indene-3-aldehyde
2-methylindene-3-aldehyde
2-methyl-5-methoxyindene-3-aldehyde
2-methyl-5-ethoxyindene-3-aldehyde
naphthalene-2-aldehyde
6-methoxynaphthalene-2-aldehyde
6-ethoxynaphthalene-2-aldehyde
5,6,7,8-tetrahydronaphthalene-1-aldehyde
4-chloro-5,6,7,8-tetrahydronaphthalene-1-aldehyde
4-fluoro-5,6,7,8-tetrahydronaphthalene-1-aldehyde
4-bromo-5,6,7,8-tetrahydronaphthalene-1-aldehyde
5,6,7,8-tetrahydronaphthalene-2-aldehyde
4-chloro-5,6,7,8-tetrahydronaphthalene-2-aldehyde
4-fluoro-5,6,7,8-tetrahydronaphthalene-2-aldehyde
4-bromo-5,6,7,8-tetrahydronaphthalene-2-aldehyde
biphenylene-2-aldehyde
7-chlorobiphenylene-2-aldehyde
7-fluorobiphenylene-2-aldehyde
7-bromobiphenylene-2-aldehyde
fluorene-2-aldehyde
7-chlorofluorene-2-aldehyde
7-fluorofluorene-2-aldehyde
7-bromofluorene-2-aldehyde
phenonthrene-2-aldehyde
7-chlorophenonthrene-2-aldehyde
7-fluorophenonthrene-2-aldehyde
7-bromophenonthrene-2-aldehyde
9,10-dihydrophenonthrene-2-aldehyde
7-chloro-9,10-dihydrophenonthrene-2-aldehyde
7-fluoro-9,10-dihydrophenonthrene-2-aldehyde
7-bromo-9,10-dihydrophenonthrene-2-aldehyde Table II β-(inden-3-yl)propenoic acid
β-(2-methylinden-3-yl)propenoic acid
β-(2-methyl-5-methoxyinden-3-yl)propenoic acid
β-(2-methyl-5-ethoxyinden-3-yl)propenoic acid
β-(naphth-2-yl)propenoic acid
β-(6-methoxynaphth-2-yl)propenoic acid
β-(6-ethoxynaphth-2-yl)propenoic acid
β-(5,6,7,8-tetrahydronaphth-1-yl)propenoic acid
β-(4-chloro-5,6,7,8-tetrahydronaphth-1-yl)propenoic acid
E β-(4-fluoro-5,6,7,8-tetrahydronaphth-1-yl)propenoic acid β-(4-bromo-5,6,7,8-tetrahydronaphth-1-yl)propenoic acid
β-(5,6,7,8-tetrahydronapth-2-yl)propenoic acid
β-(4-chloro-5,6,7,8-tetrahydronaphth-2-yl)propenoic acid
β-(4-fluoro-5,6,7,8-tetrahydronaphth-2-yl)propenoic acid
β-(4-bromo-5,6,7,8-tetrahydronaphth-2-yl)propenoic acid
β-(biphenylen-2-yl)propenoic acid
β-(7-chlorobiphenylen-2-yl) propenoic acid
β-(7-fluorobiphenylen-2-yl)propenoic acid
β-(7-bromobiphenylen-2-yl)propenoic acid
β-(fluoren-2-yl)propenoic acid
β-(7-chlorofluoren-2-yl)propenoic acid
β-(7-fluorofluoren-2-yl)propenoic acid
β-(7-bromofluoren-2-yl)propenoic acid
β-(phenanthren-2-yl)propenoic acid
β-(7-chlorophenanthren-2-yl)propenoic acid
β-(7-fluorophenanthren-2-yl)propenoic acid
β-(7-bromophenanthren-2-yl)propenoic acid
β-(9,10-dihydrophenanthren-2-yl)propenoic acid
β-(7-chloro-9,10-dihydrophenanthren-2-yl)propenoic acid
β-(7-fluoro-9,10-dihydrophenanthren-2-yl)propenoic acid
β-(7-bromo-9,10-dihydrophenanthren-2-yl)propenoic acid

EXAMPLE 2

Ethyl β-(5-Methoxynaphth-2-yl)propenoate

β-(5-methoxynaphth-2-yl)propenoic acid (0.075 moles) is allowed to reflux with 8–10 pieces of Orierite in absolute ethanol (20 ml) containing concentrated sulfuric acid (5 ml) for 21 hours. The cooled reaction mixture is diluted with chloroform and filtered hot. The filtrate is washed 3 times with water, once with 10% sodium bicarbonate and twice more with water. After drying over sodium sulfate, the solvent is removed to give ethyl β-(5-methoxynaphth-2-yl)propenoate.

When β-(5-methoxynaphth-2-yl)propenoic acid in the above example is replaced by the cinnomic acid compounds of Table II, Example 1, then the corresponding product of Table 1 is prepared.

Table I ethyl β-(inden-3-yl)propenoate
ethyl β-(2-methylinden-3-yl)propenoate
ethyl β-(2-methyl-5-methoxyinden-3-yl)propenoate
ethyl β-(2-methyl-5-ethoxyinden-3-yl)propenoate
ethyl β-(naphth-2-yl)propenoate
ethyl β-(6-methoxynaphth-2-yl)propenoate
ethyl β-(6-ethoxynaphth-2-yl)propenoate
ethyl β-(5,6,7,8-tetrahydronaphth-1-yl)propenoate
ethyl β-(4-chloro-5,6,7,8-tetrahydronaphth-1-yl)propenoate
ethyl β-(4-fluoro-5,6,7,8-tetrahydronaphth-1-yl)propenoate
ethyl β-(4-bromo-5,6,7,8-tetrahydronaphth-1-yl) propenoate
ethyl β-(5,6,7,8-tetrahydronaphth-2-yl) propenoate
ethyl β-(4-chloro-5,6,7,8-tetrahydronaphth-2-yl) propenoate
ethyl β-(4-fluoro-5,6,7,8-tetrahydronaphth-2-yl) propenoate
ethyl β-(4-bromo-5,6,7,8-tetrahydronaphth-2-yl)propenoate
ethyl β-(biphenylen-2-yl)propenoate
ethyl β-(7-chlorobiphenylen-2-yl)propenoate
ethyl β-(7-fluorobiphenylen-2-yl)propenoate
ethyl β-(7-bromobiphenylen-2-yl)propenoate
ethyl β-(fluoren-2-yl)propenoate
ethyl β-(7-chlorofluoren-2-yl)propenoate
ethyl β-(7-fluorofluoren-2-yl)propenoate
ethyl β-(7-bromofluoren-2-yl)propenoate
ethyl β-(phenanthren-2-yl)propenoate
ethyl β-(7-chlorophenanthren-2-yl)propenoate
ethyl β-(7-fluorophenanthren-2-yl)propenoate
ethyl β-(7-bromophenanthren-2-yl)propenoate
ethyl β-(9,10-dihydrophenanthren-2-yl)propenoate
ethyl β-(7-chloro-9,10-dihydrophenanthren-2-yl)propenoate
ethyl β-(7-fluoro-9,10-dihydrophenanthren-2-yl)propenoate
ethyl β-(7-bromo-9,10-dihydrophenanthren-2-yl)propenoate

EXAMPLE 3

Ethyl α,β-Dibromo-β-(5-Methoxynaphth-2-yl)propionate

A cold solution of ethyl β-(5-methoxynaphth-2-yl)propenoate (0.075 moles) in chloroform (47 ml) is brominated by the portion-wise addition of bromine (4.1 ml; 10% excess) in chloroform (10 ml) with shaking and stirring. The solution is allowed to stand at room temperature for 1¼ hours and the solvent is removed to give ethyl α,β-dibromo-β-(5-methoxynaphth-2-yl)propionate.

When ethyl β-(5-methoxynaphth-2-yl)propenoate in the above example is replaced by the cinnamote esters of Table I, Example 2, then the corresponding product of Table I below is prepared.

Table I

α,β-dibromo-β-(inden-3-yl)propionate
α,β-dibromo-β-(2-methylinden-3-yl)propionate
α,β-dibromo-β-(2-methyl-5-methoxyinden-3-yl)propionate
α,β-dibromo-β-(2-methyl-5-ethoxyinden-3-yl)propionate
α,β-dibromo-β-(naphth-2-yl)propionate
α,β-dibromo-β-(6-methoxynaphth-2-yl)propionate
α,β-dibromo-β-(6-ethoxynaphth-2-yl)propionate
α,β-dibromo-β-(5,6,7,8-tetrahydronaphth-1-yl)propionate
α,β-dibromo-β-(4-chloro-5,6,7,8-tetrahydronapth-1-yl)propionate
α,β-dibromo-β-(4-fluoro -5,6,7,8-tetrahydronaphth-1-yl)propionate
α,β-dibromo -β-(4-bromo-5,6,7,8-tetrahydronaphth-1-yl)propionate
α,β-dibromo-β-(5,6,7,8-tetrahydronaphth-2-yl)propionate
α,β-dibromo-β-(4-chloro-5,6,7,8-tetrahydronaphth-.2-yl)propionate
α,β-dibromo-β-(4-fluoro-5,6,7,8-tetrahydronaphth-2-yl)propionate
α,β-dibromo-β-(4-bromo-5,6,7,8-tetrahydronaphth-2-yl)propionate
α,β-dibromo-β-(biphenylen-2-yl)propionate
α,β-dibromo-β-(7-chlorobinphenylen -2-yl)propionate
α,β-dibromo-β7-fluorobiphenylen-2-yl)propionate
α,β-dibromo-β-(7-bromobiphenylen-2-yl)propionate
α,β-dibromo-β-(fluoren-2-yl)propionate α,β-dibromo-β-(7-chlorofluoren-2-yl)propionate
α,β-dibromo-β-(7-fluorofluoren-2-yl)propionate
α,β-dibromo-β-(7-bromofluoren-2-yl)propionate
α,β-dibromo-β-(phenanthren-2-yl)propionate
α,β-dibromo-β-(7-chlorophenanthren-2-yl)propionate
α,β-dibromo-β-(7-fluorophenanthren-2-yl)propionate
α,β-dibromo-β-(7-bromophenanthren-2-yl)propionate
α,β-dibromo-β-(9,10-dihydrophenanthren-2-yl)propionate
α,β-dibromo-β-(7-chloro-9,10-dihydrophenanthren-2-yl)propionate
α,β-dibromo-β-(7-fluoro-9,10-dihydrophenanthren-2-yl)propionate
α,β-dibromo-β-(7-bromo-9,10-dihydrophenanthren-2-yl)propionate

EXAMPLE 4

5-Methoxynaphth-2-yl propiolic Acid

Powdered ethyl α,β-dibromo-β-(5-methoxynaphth-2-yl)propionate (27.4 g) is added portion-wise to 20% ethanolic potassium hydroxide (135 ml) at room temperature. The mixture is refluxed on a steam bath for 6 hours. The alcohol is evaporated and the residue is dissolved in water and covered with ether and is acidified with cold, dilute hydrochloric acid. The ether layer is washed with water, saline, and dried over sodium sulfate. The ether is removed to give a residue which is triturated with carbon tetrachloride. Recrystallization is carried out from acetic acid-water. This material is digested and triturated with boiling carbon tetrachloride to give 5-methoxynaphth-2-yl propiolic acid.

When α,β-dibromo-β-(5-methoxynaphth-2-yl)propionate of the above example is replaced by the compounds of Table I, Example 3, then the corresponding product of Table I following is prepared.

Table I inden-3-ylpropiolic acid
2-methylinden-3-ylpropiolic acid
2-methyl-5-methoxyinden-3-ylpropiolic acid
2-methyl-5-ethoxyinden-3-ylpropiolic acid
naphth-2-ylpropiolic acid
6-methoxynaphth-2-ylpropiolic acid
6-ethoxynaphth-2-ylpropiolic acid
5,6,7,8-tetrahydronaphth-1-ylpropiolic acid
4-chloro-5,6,7,8-tetrahydronaphth-1-ylpropiolic acid
4-fluoro-5,6,7,8-tetrahydronaphth-1-ylpropiolic acid
4-bromo-5,6,7,8-tetrahydronaphth-1-ylpropiolic acid
5,6,7,8-tetrahydronaphth-2-ylpropiolic acid
4-chloro-5,6,7,8-tetrahydronaphth-2-ylpropiolic acid
4-fluoro-5,6,7,8-tetrahydronaphth-2-ylpropiolic acid
4-bromo-5,6,7,8-tetrahydronaphth-2-ylpropiolic acid
biphenylen-2-ylpropiolic acid
7-chlorobiphenylen-2-ylpropiolic acid
7-fluorobiphenylen-2-ylpropiolic acid
7-bromobiphenylen-2-ylpropiolic acid
fluoren-2-ylpropiolic acid
7-chlorofluoren-2-ylpropiolic acid
7-fluorofluoren-2-ylpropiolic acid
7-bromofluoren-2-ylpropiolic acid
phenanthren-2-ylpropiolic acid
7-chlorophenanthren-2-ylpropiolic acid
7-fluorophenanthren-2-ylpropiolic acid
7-bromophenanthren-2-ylpropiolic acid
9,10-dihydrophenanthren-2-ylpropiolic acid
7-chloro-9,10-dihydrophenanthren-2-ylpropiolic acid
7-fluoro-9,10-dihydrophenanthren-2-ylpropiolic acid
7-bromo-9,10-dihydrophenanthren-2-ylpropiolic acid

EXAMPLE 5

2-Ethynyl-5-Methoxynaphthalene 5-methoxynaphth-2-ylpropiolic acid (5.85) is heated at 120–124° for 5 hours in quinoline. The reaction product is diluted with water and washed thoroughly with dilute hydrochloric acid. This is followed by washing with sodium bicarbonate (10%). The material is passed through a short aluminum ($H^+$) column, eluted with N-hexane to give a fraction free of carbonyl absorption (I.R.). Removal of solvent gives 2-ethynyl-5-methoxynaphthalene.

When 5-methoxynaphth-2-ylpropiolic acid of the above example is replaced by the propiolic acid compounds of Table I, Example 4, then the corresponding product of Table I below is prepared.

Table I 3-ethynylindene
2-methyl-3-ethynylindene
2-methyl-3-ethynyl-5-methoxyindene
2-methyl-3-ethynyl-5-ethoxyindene
2-ethynylnaphthalene
2-ethynyl-6-methoxynaphthalene
2-ethynyl-6-ethoxynaphthalene
1-ethynyl-5,6,7,8-tetrahydronaphthalene
1-ethynyl-4-chloro-5,6,7,8-tetrahydronaphthalene
1-ethynyl-4-fluoro-5,6,7,8-tetrahydronaphthalene
1-ethynyl-4-bromo-5,6,7,8-tetrahydronaphthalene
2-ethynyl-5,6,7,8-tetrahydronaphthalene
2-ethynyl-4-chloro-5,6,7,8-tetrahydronaphthalene
2-ethynyl-4-fluoro-5,6,7,8-tetrahydronaphthalene
2-ethynyl-4-bromo-5,6,7,8-tetrahydronaphthalene
2-ethynylbiphenylene
2-ethynyl-7-chlorobiphenylene
2-ethynyl-7-fluorobiphenylene
2-ethynyl-7-bromobiphenylene
2-ethynylfluorene
2-ethynyl-7-chlorofluorene
2-ethynyl-7-fluorofluorene
2-ethynyl-7-bromofluorene
2-ethynylphenanthrene
2-ethynyl-7-chlorophenanthrene
2-ethynyl-7-fluorophenanthrene
2-ethynyl-7-bromophenanthrene
2-ethynyl-9,10-dihydrophenanthrene
2-ethynyl-7-chloro-9,10-dihydrophenanthrene
2-ethynyl-7-fluoro-9,10-dihydrophenanthrene
2-ethynyl-7-bromo-9,10-dihydrophenanthrene

EXAMPLE 6

2-Ethynyl-5-Methoxynaphthalene

Methyl (5-methoxynaphth-2-yl)ketone (0.25 moles) and phosphorus pentachloride (0.31 moles) are placed in a 3-neck flask equipped with a mechanical stirrer, a condenser connected to a nitrogen inlet, and a thermometer. The mixture is stirred at 33°–35° C for 3 days. The cooled reaction mixture is poured onto 800 g of ice and extracted with 3 × 500 ml of ether. The ether fraction is washed with 2 × 100 ml water 4 × 100 ml of 5% sodium hydroxide, 3 × 50 ml water, 2 × 50 ml of saturated saline and dried over sodium sulfate. The ether is removed to give the chlorinated intermediate. The intermediate is dissolved in anhydrous THF (200 ml) and is added dropwise to a freshly prepared solution of sodamide in liquid ammonia, using a dry-ice condenser. The reaction mixture is allowed to stir at room temperature overnight; then, it is poured into 50 ml of water and 500 ml of ether. The ether fraction is washed with 3 × 50 ml water and solvent gives a residue which is distilled to give 2-ethynyl-5-methoxynaphthalene.

When methyl (5-methoxynaphth-2-yl)ketone of the above example is replaced by the ketone starting materials of Table I, below then the corresponding product of Table I, Example 5 is prepared.

Table I methyl (inden-3-yl)ketone
methyl (2-methylinden-3-yl)ketone
methyl (2-methyl-5-methoxyinden-3-yl)ketone
methyl (2-methyl-5-ethoxyinden-3-yl)ketone
methyl (naphth-2-yl)ketone
methyl (6-methoxynaphth-2-yl)ketone
methyl (6-ethoxynaphth-2-yl)ketone
methyl (5,6,7,8-tetrahydronaphth-1-yl)ketone
methyl (4-chloro-5,6,7,8-tetrahydronaphth-1-yl)ketone
methyl (4-fluoro-5,6,7,8-tetrahydronaphth-1-yl)ketone
methyl (4-bromo-5,6,7,8-tetrahydronaphth-1-yl)ketone
methyl (5,6,7,8-tetrahydronaphth-2-yl)ketone
methyl (4-chloro-5,6,7,8-tetrahydronaphth-2-yl)ketone
methyl (4-fluoro-5,6,7,8-tetrahydronaphth-2-yl)ketone
methyl (4-bromo-5,6,7,8-tetrahydronaphth-2-yl)ketone
methyl (biphenylen-2-yl)ketone
methyl (7-chlorobiphenylen-2-yl)ketone
methyl (7-fluorobiphenylen-2-yl)ketone
methyl (7-bromobiphenylen-2-yl)ketone
methyl (fluoren-2-yl)ketone
methyl (7-chlorofluoren-2-yl)ketone
methyl (7-fluorofluoren-2-yl)ketone
methyl (7-bromofluorene-2-yl)ketone
methyl (phenanthren-2-yl)ketone
methyl (7-chlorophenanthren-2-yl)ketone
methyl (7-fluorophenanthren-2-yl)ketone
methyl (7-bromophenanthren-2-yl)ketone
methyl (9,10-dihydrophenanthren-2-yl)ketone
methyl (7-chloro-9,10-dihydrophenanthren-2-yl)ketone
methyl (7-fluoro-9,10-dihydrophenanthren-2-yl)ketone
methyl (7-bromo-9,10-dihydrophenanthren-2-yl)ketone

I claim:

1. A compound of the formula

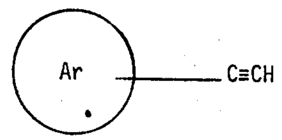

where

Ar is

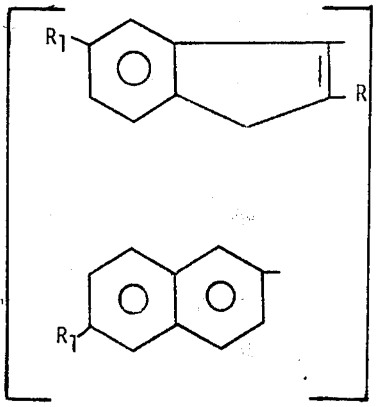

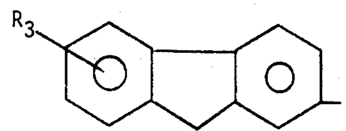

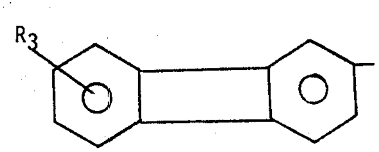

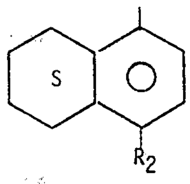

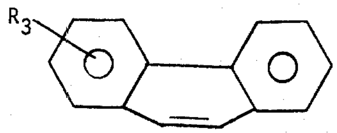

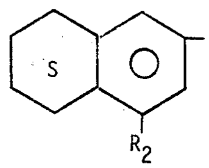

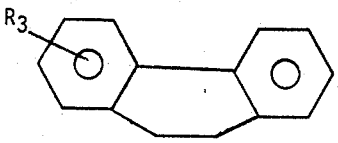

where $R_2$ is halo and $R_3$ is halo.

2. The compound of claim 1 which is 2-ethynyl-4-chloro-5,6,7,8-tetrahydronaphthalene.

3. The compound of claim 1 which is 2-ethynyl-4-fluoro-5,6,7,8-tetrahydronaphthalene.

4. The compound of claim 1 which is 2-ethynyl-4-bromo-5,6,7,8-tetrahydronaphthalene.

5. The compound of claim 1 which is 1-ethynyl-4-chloro-5,6,7,8-tetrahydronaphthalene.

6. The compound of claim 1 which is 1-ethynyl-4-fluoro-5,6,7,8-tetrahydronaphthalene.

7. The compound of claim 1 which is 1-ethynyl-4-bromo-5,6,7,8-tetrahydronaphthalene.

* * * * *